US005304686A

United States Patent [19]
Slaugh et al.

[11] Patent Number: 5,304,686
[45] Date of Patent: Apr. 19, 1994

[54] PROCESS FOR MAKING 3-HYDROXYPROPANAL AND 1,3-PROPANEDIOL

[75] Inventors: Lynn H. Slaugh, Houston; Juan P. Arhancet, Katy, both of Tex.

[73] Assignee: Shell Oil Company, Houston, Tex.

[21] Appl. No.: 91,107

[22] Filed: Jul. 13, 1993

[51] Int. Cl.$^5$ ............................................. C07C 47/19
[52] U.S. Cl. ............................... 568/496; 568/454; 568/852; 568/867
[58] Field of Search ............ 568/454, 867, 852, 449, 568/420; 560/179

[56] References Cited
U.S. PATENT DOCUMENTS

| | | | |
|---|---|---|---|
| 3,401,204 | 9/1968 | Mason et al. | 260/606.5 |
| 3,456,017 | 7/1969 | Smith et al. | 260/602 |
| 3,463,819 | 8/1969 | Smith et al. | 260/602 |
| 3,527,818 | 9/1970 | Mason et al. | 260/632 |
| 3,687,981 | 8/1972 | Lawrence et al. | 260/340.7 |
| 4,873,378 | 9/1989 | Murphy et al. | 568/867 |
| 4,873,379 | 9/1989 | Murphy et al. | 568/867 |
| 4,935,554 | 6/1990 | Murphy et al. | 568/867 |
| 5,030,766 | 9/1991 | Briggs | 568/496 |

*Primary Examiner*—Werren B. Lone

[57] ABSTRACT

This invention relates to a process for making 3-hydroxypropanal by intimately contacting
(a) ethylene oxide,
(b) ditertiary phosphine-modified cobalt carbonyl catalyst, said phosphine being a hydrocarbylene-bis(monophosphabicyclononane) in which each phosphorus atom is joined to hydrocarbylene and is a member of a bridge linkage without being a bridgehead atom and which hydrocarbylene-bis(monophosphabicyclononane) has 18 to 50 carbon atoms, 8 carbon atoms thereof together with a phosphorus atom being members of each of the two bicyclic skeletal structures,
(c) a catalyst promoter comprising an acid and a metal salt promoter selected from a salt of a metal of Group IIA, Group IIB, Group IIIB and the Rare Earth Series of the Periodic Table of the Elements (CAS version),
(d) carbon monoxide, and
(e) hydrogen, the molar ratio of carbon monoxide to hydrogen being from about 4:1 to about 1:6, in liquid-phase solution in an inert reaction solvent, at a temperature of from about 30° C. to about 150° C. and a pressure of from about 50 psi to about 10,000 psi. The use of the acid/metal salt promoter enhances the activity of the catalyst.

20 Claims, No Drawings

PROCESS FOR MAKING 3-HYDROXYPROPANAL AND 1,3-PROPANEDIOL

FIELD OF THE INVENTION

This invention relates to a process for making 3-hydroxypropanal hydroformylating ethylene oxide using ditertiary phosphine-modified cobalt carbonyl catalysts in the presence of acid and salt promoters. The 3-hydroxypropanal is converted to 1,3-propanediol by hydrogenation.

BACKGROUND OF THE INVENTION

3-Hydroxypropanal is a useful chemical intermediate. It can be readily converted to 1,3-propanediol which finds use as an intermediate in the production of polyester fibers and films.

U.S. Pat. No. 3,463,819 and No. 3,456,017 teach a process for the hydroformylation of ethylene oxide to produce 1,3-propanediol and 3-hydroxypropanal using a tertiary phosphine-modified cobalt carbonyl catalysts.

U.S. Pat. No. 3,687,981 uses cobalt octacarbonyl as a catalyst and discloses hydroquinone as a catalyst stabilizer in the hydroformylation of ethylene oxide. Inorganic halogen-containing compounds, such as hydrochloric acid and potassium chloride, are disclosed hydroformylation promoters, i.e., compounds that increase the conversion of ethylene oxide to the desired product. Trace amounts are said to be useful.

In U.S. Pat. No. 3,401,204 and No. 3,527,818 ditertiary phosphine ligands and cobalt catalysts prepared therefrom are described as being suitable for hydroformylating olefins to alcohols.

It is an object of this invention to use an improved cobalt-ditertiary phosphine ligand catalyst in combination with a particular catalyst promoter system to hydroformylate ethylene oxide to 3-hydroxypropanal in high yield, which 3-hydroxypropanal can then be hydrogenated with hydrogen to 1,3-propanediol in substantially quantitative yield using conventional hydrogenation catalysts.

SUMMARY OF THE INVENTION

This invention relates to a process for making 3-hydroxypropanal which comprises intimately contacting (a) ethylene oxide
(b) ditertiary phosphine-modified cobalt carbonyl catalyst, said phosphine being a hydrocarbylene-bis(-monophosphabicycloalkane) in which each phosphorus atom is joined to hydrocarbylene and is a member of a bridge linkage without being a bridgehead atom and which hydrocarbylene-bis(monophosphabicycloalkane) has 11 to 300 carbon atoms, 5 to 12 carbon atoms thereof together with a phosphorus atom being members of each of the two bicyclic skeletal structures,
(c) a catalyst promoter comprising an acid and a metal salt selected from a salt of a metal of Group IIA, Group IIB, Group IIIB and the Rare Earth Series of the Periodic Table of the Elements,
(d) carbon monoxide, and
(e) hydrogen, the molar ratio of carbon monoxide to hydrogen being from about 4:1 to about 1:6, in liquid-phase solution in an inert reaction solvent, at a temperature of from about 30° C. to about 150° C. and a pressure of from about 50 psi to about 10,000 psi. Optionally, the product comprising 3-hydroxypropanal is hydrogenated with hydrogen in the presence of a hydrogenation catalyst to convert the aldehyde and aldehyde oligomers to 1,3-propanediol.

DESCRIPTION OF THE PREFERRED EMBODIMENTS

Ethylene oxide is hydroformylated by reaction with carbon monoxide and hydrogen in the presence of a ditertiary phosphine-modified cobalt carbonyl catalyst. The reaction products comprise primarily 3-hydroxypropanal (and oligomers thereof) and small amounts of 1,3-propanediol. The ratio of the two products can be adjusted by adjusting the amount of catalyst present in the reaction mixture, the amount of hydrogen present or the temperature of the reaction. When the term "3-hydroxypropanal" is used herein is understood to mean the monomer as well as dimers, such as 2-(2-hydroxyethyl)-4-hydroxy-1,3-dioxane, as well as trimers and higher oligomers of 3-hydroxypropanal. In a preferred embodiment, lower amounts of catalyst are used to produce primarily the aldehyde and its oligomers which are then hydrogenated to the 1,3-propanediol in a separate hydrogenation step using a conventional hydrogenation catalyst and hydrogen. The use of the particular ditertiary phosphines as complexing ligands for the cobalt catalyst results in catalysts providing very high yields of hydroformylated products, higher than that provided by the use of conventional phosphine ligands. The use of the particular catalyst promoting system of this invention provides for a more active catalyst which results in more ethylene oxide being converted to product aldehyde and diol.

The process is conducted, in one modification, by charging the epoxide reactant, catalyst, catalyst promoter(s) and reaction solvent to an autoclave or similar pressure reactor and introducing the hydrogen and carbon monoxide while the reaction mixture is maintained at reaction temperature. Alternatively, the process is conducted in a continuous manner as by contacting the reactants, catalyst and catalyst promoter(s) during passage through a reactor which is typically tubular in form. For best results the process is conducted under conditions of elevated temperature and pressure. Reaction temperatures range from about 30° C. to about 150° C., preferably from about 50° C. to about 125° C. being preferred, and most preferably from about 70° C. to about 110° C. The reaction pressure is desirably in the range of from about 50 p.s.i. to about 10,000 p.s.i., preferably from about 500 p.s.i. to about 3000 p.s.i. In one modification of the process, inert gaseous diluent is present, e.g., inert gaseous diluents such as argon, helium, methane, nitrogen and the like, in which case the reaction pressure is properly considered to be the sum of the partial pressures of the materials other than diluent. In the preferred modification of the process, however, the reaction is conducted in the substantial absence of added diluent.

The course of the reaction is easily followed by observing the pressure decrease within the reactor, by in situ infrared absorption techniques or by periodic withdrawal and analysis of samples from the reaction system. At the conclusion of reaction, the product mixture is separated by conventional methods such as selective extraction, fractional distillation, decantation, selective crystallization and the like. The unreacted starting material as well as the catalyst and reaction solvent are suitably recycled for further reaction.

The catalysts employed in the process of the invention are ditertiary phosphine-modified cobalt carbonyl complexes. As is discussed in greater detail hereinbelow, the ditertiary phosphine complexing ligand portion of the catalyst complex comprises a hydrocarbylene-bis(monophosphabicycloalkane) in which each phosphorus atom is joined to hydrocarbylene and is a member of a bridge linkage without being a bridgehead atom and which hydrocarbylene-bis(monophosphabicycloalkane) has 11 to about 300 carbon atoms, preferably 11 to about 200, more preferably 11 to about 100 and most preferably 18 to about 80 carbon atoms; 5 to 12, preferably 6 to 12, more preferably 7 to 12 and most preferably 8 carbon atoms thereof together with a phosphorus atom being members of each of the two bicyclic skeletal structures. Particularly preferred ditertiary phosphines are chosen from α,ω-hydrocarbylene-P,P'-bis(monophosphabicyclononanes) in which ring systems (a) each phosphorus atom is a member of a bridge linkage, (b) each phosphorus atom is not in a bridgehead position, and (c) each phosphorus atom is not a member of the bicyclic system of the other, and (d) the smallest phosphorus-containing rings contain at least five atoms. The hydrocarbylene is preferably selected from ethylene, propylene and butylene. Most preferably the hydrocarbylene is ethylene and each of the monophosphabicyclononane moieties of the ditertiary phosphine is independently selected from 9-phosphabicyclo[4.2.1]nonane and 9-phosphabicyclo[3.3.1]nonane. As used herein the term "9-phosphabicyclononyl" or "9-phosphabicyclononane" will refer to phosphabicyclo[4.2.1]nonane and 9-phosphabicyclo[3.3.1]nonane moieties and mixtures thereof.

In general terms the ditertiary phosphine ligands used to form the cobalt-carbonyl-ditertiary phosphine complexes comprise bicyclic heterocyclic ditertiary phosphines. They are hydrocarbylene-connected monophosphabicycloalkanes in which the smallest phosphorus-containing rings contain at least four, preferably at least five atoms, and the phosphorus atom therein is a member of a bridge linkage but is not a bridgehead atom. In addition to the hydrocarbylene substitution on the phosphorus atoms, the ring carbons may also be substituted. One class of such compounds has from 11 to about 300, preferably 11 to about 200, more preferably 11 to about 100 and most preferably 18 to about 80 carbon atoms, and is represented by the formula

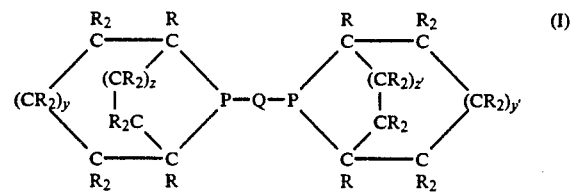

where Q represents hydrocarbylene; R independently represents hydrogen and hydrocarbyl of 1 to about 30 carbon atoms; y and z represent zero or positive integers whose sum is from 0 to 7; y' and z', independent of the values of y and z, represent zero or positive integers whose sum is from 0 to 7. Preferably y and z represent positive integers whose sum is from 1 to 7, more preferably from 2 to 7 and preferably 3 with each of which having a minimum value of 1, y' and z', independent of the values of y and z, represent positive integers whose sum is from 1 to 7, preferably from 2 to 7 and preferably 3 with each of which having a minimum value of 1.

Hence, a preferred group of bicyclic heterocyclic ditertiary phosphines includes those represented by Formula I where Q represents hydrocarbylene of 2 to 30 carbon atoms and especially of 2 to 20; y and z represent positive integers whose sum is 3 and each of which has a minimum value of 1; y' and z', independent of the values of y and z, represent positive integers whose sum is 3 and each of which has minimum value of 1; and R represents hydrogen and optionally hydrocarbyl of from 1 to 20 carbon atoms.

The term "hydrocarbylene" is used in its accepted meaning as representing a diradical formed by removal of two hydrogen atoms from carbon atoms of a hydrocarbon or preferably one hydrogen atom from each of two different carbon atoms of a hydrocarbon. The hydrocarbylene groups represented by Q in the formula above may be any nonacetylenic acyclic or cyclic organic radical composed solely of carbon and hydrogen. Wide variation is possible in that the (nonacetylenic) acyclic or cyclic hydrocarbylene group may be arene, alkylene, alkenylene, aralkylene, cycloalkylene, straight chain, branched chain, large or small. Representative hydrocarbylene groups include ethylene, trimethylene, tetramethylene, butylene, pentamethylene, pentylene, methylpentylene, hexamethylene, hexenylene, ethylhexylene, dimethylhexylene, octamethylene, octenylene, cyclooctylene, methylcyclooctylene, dimethylcyclooctylene, isooctylene, dodecamethylene, hexadecenylene, octadecamethylene, eicosamethylene, hexacosamethylene, triacontamethylene, phenylenediethylene, and the like. A particularly useful class of bicyclic heterocyclic ditertiary phosphines is that containing only carbon, hydrogen, and phosphorus atoms. Substituted hydrocarbylene groups are also contemplated and may contain a functional group such as the carbonyl, carboxyl, nitro, amino, hydroxy (e.g. hydroxyethyl), cyano, sulfonyl, and sulfoxyl groups. A particularly useful group of ditertiary phosphines consists of those in which Q is hydrocarbylene of up to about 30 carbon atoms, preferably from 2 to 30 carbon atoms; more preferably from 2 to 20 carbons, even more preferably from 2 to 10. In a preferred embodiment Q is ethylene, propylene or butylene, more preferably ethylene.

The term "hydrocarbyl" is used in its accepted meaning as representing a radical formed by removal of one hydrogen atom from a carbon atom of a hydrocarbon. The hydrocarbyl groups represented by R in the formula above may be any nonacetylenic acyclic or cyclic organic radical composed solely of carbon and hydrogen. Wide variation is possible in that the (nonacetylenic) acyclic or cyclic hydrocarbyl group may be aryl, alkyl, alkenyl, aralkyl, cycloalkyl, straight chain, branched chain, large or small. Representative hydrocarbyl groups include methyl, ethyl, butyl, pentyl, methylpentyl, hexenyl, ethylhexyl, dimethylhexyl, octamethyl, octenyl, cyclooctyl, methylcyclooctyl, dimethylcyclooctyl, isooctyl, dodecyl, hexadecenyl, octyl, eicosyl, hexacosyl, triacontyl, phenylethyl, and the like. Substituted hydrocarbyl groups are also contemplated and may contain a functional group such as the carbonyl, carboxyl, nitro, amino, hydroxy (e.g. hydroxyethyl), cyano, sulfonyl, and sulfoxyl groups. Preferably R is hydrogen or hydrocarbyl, preferably alkyl, having 1 to about 30, preferably 1 to about 20 and most preferably from 8 to 20 carbon atoms.

Ditertiary phosphine ligands and cobalt catalysts prepared therefrom are known in the art and their method of preparation are described in detail in U.S. Pat. Nos. 3,401,204 and 3,527,818, which are both incorporated by reference herein.

The phosphine ligands may also be partially oxidized to phosphine oxides in order to enhance the activity of the cobalt-ligand complex. The oxidation is carried out with an oxidant under mild oxidizing conditions such that an oxygen will bond to a phosphorus, but phosphorus-carbon, carbon-carbon and carbon-hydrogen bonds will not be disrupted. By suitable selection of temperatures, oxidants and oxidant concentrations such mild oxidation can occur. The oxidation of the phosphine ligands is carried out prior to the forming of the catalyst complex.

Suitable oxidizing agents include peroxy-compounds, persulfates, permanganates, perchromates and gaseous oxygen. Preferred compounds, for ease of control, are the peroxy-compounds. Peroxy-compounds are those which contain the peroxy (—O—O—) group. Suitable peroxy-compounds may be inorganic or organic. Suitable inorganic compounds include hydrogen peroxide as well as inorganic compounds which in contact with water liberate hydrogen peroxide, such compounds include the mono-valent, di-valent and trivalent metal peroxides as well as hydrogen peroxide addition compounds. Also suitable are the organic peroxy-compounds, including hydroperoxides; α-oxy- and α-peroxy-hydroperoxides and peroxides; peroxides; peroxyacids; diacyl peroxides; and peroxyesters. Suitable peroxyorgano-compounds include t-butyl hydroperoxide, cumene hydroperoxide, dibenzoyl peroxide and peroxyacetic acid. Peroxy-compounds suitable for carrying out the oxidation process are known in the art, and suitable examples can be found in The Encyclopedia of Chemical Technology, Vol. 17, pp. 1–89, Third Edition (John Wiley & Sons, 1982), incorporated by reference herein.

Typically oxidation is carried out by adding to the ligand a measured amount of oxidizing agent, sufficient to carry out the degree of oxidation required. The ligand may be dissolved in a suitable solvent. The oxidizing agent is typically added slowly over a period of time to control the oxidizing conditions. The temperature is maintained to provide mild oxidizing conditions. When hydrogen peroxide is used as the oxidizing agent, the temperature is typically maintained at room temperature.

The oxidation of the ligand is carried out to provide no more than about 0.5 oxygen atoms per phosphorus atoms, on the average, in the oxidized ligand product. Preferably the ratio of oxygen atoms to phosphorus atoms in the oxidized ligand will range, on the average, from about 0.01:1 to about 0.5:1, and more preferably from about 0.05:1 to about 0.3:1.

The catalysts can be prepared by a diversity of methods. A convenient method is to combine a cobalt salt, organic or inorganic, with the desired ditertiary phosphine ligand, for example, in liquid phase followed by reduction and carbonylation. Suitable cobalt salts comprise, for example, cobalt carboxylates such as acetates, octanoates, etc., which are preferred, as well as cobalt salts of mineral acids such as chlorides, fluorides, sulfates, sulfonates, etc. Operable also are mixtures of these cobalt salts. It is preferred, however, that when mixtures are used, at least one component of the mixture be cobalt alkanoate of 6 to 12 carbon atoms. The valence state of the cobalt may be reduced and the cobalt-containing complex formed by heating the solution in an atmosphere of hydrogen and carbon monoxide. The reduction may be performed prior to the use of the catalysts or it may be accomplished simultaneously with the hydroformylation process in the hydroformylation zone. Alternatively, the catalysts can be prepared from a carbon monoxide complex of cobalt. For example, it is possible to start with dicobalt octacarbonyl and, by heating this substance with a suitable ditertiary phosphine ligand, the ligand replaces one or more, preferably at least two, of the carbon monoxide molecules, producing the desired catalyst. When this latter method is executed in a hydrocarbon solvent, the complex may be precipitated in crystalline form by cooling the hot hydrocarbon solution. This method is very convenient for regulating the number of carbon monoxide molecules and phosphine ligand molecules in the catalyst. Thus, by increasing the proportion of phosphine ligand added to the dicobalt octacarbonyl, more of the carbon monoxide molecules are replaced.

The optimum ratio of ethylene oxide feed to ditertiary phosphine-modified cobalt carbonyl complex will in part depend upon the particular cobalt complex employed. However, molar ratios of ethylene oxide to cobalt complex from about 2:1 to about 10,000:1 are generally satisfactory, with molar ratios of from about 50:1 to about 500:1 being preferred. When batch processes are used, it is understood that the above ratios refer to the initial starting conditions. In one modification, the ditertiary phosphine-modified cobalt carbonyl complex is employed as a preformed material, being prepared as by reaction of a cobalt salt with carbon monoxide and hydrogen in the presence of the ditertiary phosphine ligand, then isolated and subsequently utilized in the present process. In an alternate modification, the ditertiary phosphine-modified cobalt complex is prepared in situ as by addition to the reaction mixture of a cobalt salt or cobalt octacarbonyl together with the ditertiary phosphine ligand whose introduction into the catalyst complex is desired.

In practice, it is preferable to employ the ditertiary phosphine-modified cobalt complex in conjunction with a minor proportion of excess ditertiary phosphine ligand which is the same as or is different from the ditertiary phosphine ligand(s) of the cobalt complex. Although the role of the excess phosphine is not known with certainty, the presence thereof in the reaction system appears to promote or otherwise modify catalyst activity. Phosphorus:cobalt atom ratios utilized in conjunction with the catalyst complex will range from about 0.5:1 to about 2:1, preferably from about 1:1 to about 1.5:1. A ratio of about 1.25:1 is particularly preferred.

The process of the invention is conducted in liquid-phase solution in an inert solvent. A variety of solvents which are inert to the reactants and catalyst and which are liquid at reaction temperature and pressure are in part operable. Illustrative of suitable solvent are hydrocarbons, particularly aromatic hydrocarbons of up to 16 carbon atoms such as benzene, toluene, xylene, ethylbenzene, and butylbenzene; alkanes such as hexanes, octanes, dodecanes, etc.; alkenes such as hexenes, octenes, dodecenes, etc.; alcohols such as t-butyl alcohol, hexanol, dodecanol, including alkoxylated alcohols; nitriles such acetonitrile, propionitrile, etc.; ketones, particularly wholly aliphatic ketones, i.e., alkanones, of up to about 16 carbon atoms such as acetone, methyl ethyl ketone, diethyl ketone, methyl isobutyl ketone, ethyl hexyl ketone and dibutyl ketone; esters of up to 16 carbon atoms, particularly lower alkyl esters of carboxylic acids which are aliphatic or aromatic carboxylic acids having one or more carboxyl groups, preferably from 1 to 2, such as ethyl acetate, methyl propionate, propyl butyrate, methyl benzoate, diethyl glutarate, diethyl phthalate and dimethyl terephthalate; and ethers of up to about 16 carbon atoms and up to 4 ether oxygen atoms, which ethers are cyclic or acyclic ethers and which are wholly aliphatic ethers, e.g., diethyl ether, diisopropyl ether, dibutyl ether, ethyl hexyl ether, methyl octyl ether, dimethoxyethane, diethylene glycol dimethyl ether, diethylene glycol diethyl ether, diethylene glycol dibutyl ether, tetraglyme, glycerol trimethyl ether, 1,2,6-trimethoxyhexane, tetrahydrofuran, 1,4-dioxane, 1,3-dioxane, 1,3-dioxoland and 2,4-dimethyl-1,3-dioxane, or which are at least partially aromatic, e.g., diphenyl ether, phenylmethyl ether, 1-methylnaphthalene, phenylisopropyl ether, halogenated hydrocarbons, such as chlorobenzene, dichlorobenzene, fluorobenzene, methyl chloride, methylene dichloride. Mixtures of solvents can also be utilized.

The amount of solvent to be employed is not critical. Typical molar ratios of reaction solvent to ethylene oxide reactant vary from about 5:1 to about 150:1.

Suitable selection of solvents can enhance product recovery. By selecting solvents with suitable polarity, a two phase system will form upon cooling of the reaction mixture with selective distribution of the catalyst and ligand in one phase and product 3-hydroxypropanal and 1,3-propanediol in a second phase. This will allow for easier separation of catalyst and ligand and recycle thereof back to the reactor. When a two phase separation process is used, solvents that would not be desirable in the reaction mixture, such as water and acids, can be used to enhance distribution of product to one phase and catalyst/ligand to the other phase.

Illustrative solvents for use in a one phase system are diethylene glycol, tetraglyme, tetrahydrofuran, t-butyl alcohol, and dodecanol. Illustrative solvents for use to provide a two phase system upon cooling are toluene, 1-methylnaphthalene, xylenes, diphenyl ether and chlorobenzene.

The process of the invention comprises contacting the ethylene oxide reactant, catalyst and catalyst promoter and with carbon monoxide and molecular hydrogen. The molar ratio of carbon monoxide to hydrogen most suitably employed is from about 4:1 to about 1:6, with best results being obtained when ratios of from about 1:1 to about 1:4 are utilized. No special precautions need to be taken with regard to the carbon monoxide and hydrogen and commercial grades of these reactants are satisfactory. The carbon monoxide and hydrogen are suitable employed as separate materials although it is frequently advantageous to employ commercial mixtures of these materials, e.g., synthesis gas.

A key aspect of the instant invention is the use of a special combination of catalyst promoters to increase the activity of the catalyst. The addition of small amounts of acids and selected metal salts to the hydroformylation reaction mixture can enhance or promote the conversion of ethylene oxide by increasing the activity of the catalyst. Acids are defined herein to mean those compounds which can donate a proton under reaction conditions.

Suitable acids can include inorganic acids such HCl, HBr, HI, boric acid and organic acids in amounts ranging from trace amounts up to about two times the molar amount of catalyst utilized. Suitable organic acids include the organo-acids having carbon numbers of 1 to about 16, such as carboxylic acids, sulfonic acids, phosphonic acids, phosphinic acids as well as other organic compounds that will donate protons under reaction conditions such as imidazole, benzoimidazole, pyridinium salts, pyrazinium salts, pyrimidinium salts, particularly salts of the aforementioned acids. Non-limiting examples of organic acids include acetic acid, propionic acid, hexanoic acid, 2-ethylhexanoic acid, octanoic acid, 3-(phenylsulfonyl)propionic acid, para-toluenesulfonic acid, 2-carboxyethylphosphonic acid, ethylphosphonic acid, n-butylphosphonic acid, t-butylphosphonic acid, phenylphosphonic acid, phenylphosphenic acid, phenyl boric acid, pyridinium para-toluenesulfonate and pyridinium octoate. Another suitable method for providing promoter acids is to use as a catalyst precursor a cobalt salt of an organic acid, which will convert to cobalt carbonyl and the organic acid under reaction conditions. Such precursor salts include cobalt acetate, cobalt 2-ethylhexanoate, cobalt benzoate, cobalt formate and cobalt oleate. The ratio of gram equivalents of acid promoter to gram atoms of cobalt in the catalyst present in the reaction mixture will generally range from about 0.001:1 to about 4:1, preferably from about 0.01:1 to about 2:1.

Promoting amounts of one or more metal salts selected from a salt of a metal of Group IIA, Group IIB, Group IIIB and the Rare Earth Series of the Periodic Table of the Elements (CAS version) are also added to the reaction mixture along with the promoting amounts of acid. Group IIA comprises the alkaline earth metals, calcium through barium; Group IIB comprises zinc, cadmium and mercury; Group IIIB comprises scandium, yttrium and lanthanum; and the Rare Earth Group comprises cerium through lutetium. Any metal salt from the aforementioned Groups that is at least partially soluble in the reaction mixture is suitable. Both inorganic salts and organic salts are suitable. Included in the inorganic salts are halides, chromates, sulfates, borates, carbonates, bicarbonates, chlorates, phosphates, etc. Particularly desirable organic salts are salts of carboxylic acids having carbon numbers ranging from 1 to about 20. Examples of metal salts that have been found suitable as copromoters include halides, such as bromides, iodides, and chlorides, carboxylates, such as acetates, propionates and octoates, borates, nitrates, sulfates and the like. In general a metal salt that does not react with ethylene oxide, the reaction solvent or the hydroformylation products is suitable as copromoters with acids. The ratio of gram equivalents of metal of the salt promoter to gram atoms of cobalt in the catalyst present in the reaction mixture will generally range from about 0.001:1 to about 2:1, preferably from about 0.01:1 to about 1:1, and more preferably from about 0.1:1 to about 0.5:1.

In a preferred embodiment the product of the hydroformylation reaction is further hydrogenated to produce a product comprising substantially 1,3-propanediol. The hydroformylated product is preferably separated from the catalyst before being hydrogenated. Inert solvent may be added to the product prior to hydrogenation, or, if an inert (to hydrogenation) solvent was used in the hydroformylation reaction, it may be separated with the product and passed to the hydrogenation reactor. The hydrogenation catalyst can be any of the well known hydrogenation catalysts used in the art such as Raney nickel, palladium, platinum, ruthenium, rhodium, cobalt and the like. It is desirable to employ as the hydrogenation catalyst a metal or a compound of a metal which may be easily and economically prepared, which has a high degree of activity, and retains this activity for extended periods of time. The hydrogenation catalyst may be employed homogeneously, in a finely divided form and dispersed throughout the reaction mixture, or preferably it may be employed on a support or carrier material such as alumina, carbon or the like. Preferred catalysts are Raney nickel and supported platinum, particularly platinum on carbon. Hydrogenation conditions include pressures ranging from 50–10,000 psi and temperatures ranging from 30° C. to 175° C. The hydrogenating gas used is molecular hydrogen or a mixture of hydrogen and carbon monoxide such as that used for the hydroformylation reaction.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

Illustrative Embodiment I

In the examples and tables the following definitions are used:
"PDO" is 1,3-propanediol.
"3-HPA" is 3-hydroxypropanal.
"PDO Precursors" are those compounds which upon hydrogenation produce PDO and include primarily 3-hydroxypropanal. Also included are small amounts of acrolein. Most of the acrolein is an artifact of the GC measuring process as a result of decomposition of 3-hydroxypropanal during analysis. In situ infrared spectroscopic analyses after completion of the hydroformylation reactions showed no acrolein present in the products. Lowering the temperature and chemically passifying the injection port of the GC instrument dramatically lowered these artifact peak heights, indicating that it is at most only a minor product (1–2%). The product "oligomers" include dimers, trimers and other oligomers of 3-hydroxypropanal which can be hydrogenated to propanediol.

In this illustrative embodiment catalysts complexed with the preferred ligands promoted by the acid/salt promoter of the instant invention are prepared and tested for hydroformylation of ethylene oxide and compared with catalysts which are not promoted by the promoter system of the instant invention.

In Situ Catalyst Preparation and Hydroformylation

In an inert atmosphere, a 100 ml air-stirred Parr autoclave was charged with 228 mg (0.66 mmole) of cobalt 2-ethylhexanoate, 155 mg (0.50 mmole) of 1,2-bis(9-phosphabicyclononyl)ethane, 33 mg (0.21 mmole) of calcium acetate and 23 ml of dry, nitrogen-purged toluene-chlorobenzene solution (5:1 volume ratio). The autoclave was sealed and pressured to 1300 psig with a hydrogen-carbon monoxide gas mixture (1:1 molar ratio). The reaction was stirred and heated at 130° C. for 30 minutes at 1500 psig. The reactor was then cooled to an internal temperature of 5° C. and the gases were vented to leave the autoclave at ambient pressure.

Ethylene oxide (5 gm, 113 mmole) was added to the reactor and the reactor was then heated and stirred for 3 hours at 90° C. at a pressure of 1400–1500 psig of hydrogen-carbon monoxide gas (1:1 molar ratio).

After cooling to 5° C., the reactor was purged with nitrogen and the two-phase product mixture was collected to give about 29 grams of solvent phase and about 2 grams of an oil phase. The two phases were independently analyzed by gas chromatography. Results are shown in Table 1 as example 5.

The above example was repeated using differing amounts of promoter salt and different promoter salts with the difference that a reaction time of 1.5 rather than 3 hours was used for examples 7 through 12. The results are shown in Table 1.

Example Comp 1 in Table 1 is a comparative example carried out in the same fashion as above, but without the salt promoter.

TABLE 1

| Example | Co-Promoter Source[a] | Amount (mmoles) | EO[b] Conv. Rate | EO Conv., Mole % | CH₃CHO | Selectivity, 3-HPA[c] | Mole % Oligomers |
|---|---|---|---|---|---|---|---|
| 1 | Mg | 0.11 | 0.89 | 48.4 | 1.2 | 34.1 | 64.8 |
| 2 | Mg | 0.21 | 0.73 | 44.8 | 0.9 | 33.8 | 65.3 |
| 3 | Ca | 0.05 | 0.62 | 34.2 | 0.9 | 99.1 | — |
| 4 | Ca | 0.11 | 0.60 | 33.7 | 0.8 | 98.1 | 1.1 |
| 5 | Ca | 0.21 | 0.68 | 37.8 | 0.9 | 97.7 | 1.4 |
| 6 | Sn | 0.21 | 0.54 | 29.8 | 14.2 | 83.6 | 2.2 |
| 7 | Zn | 0.21 | | 32.0 | 2.1 | 94.2 | 3.7 |
| 8 | Y | 0.21 | | 36.3 | 3.3 | 96.4 | — |
| 9 | La | 0.21 | | 27.3 | 4.3 | 95.7 | — |
| 10 | Eu | 0.21 | | 43.7 | 2.5 | 96.8 | — |
| 11 | Er | 0.21 | | 38.9 | 1.9 | 98.1 | — |
| 12 | Yb | 0.21 | | 32.9 | 3.6 | 96.4 | — |
| Comp. 1 | None | -0- | 0.24 | 13.1 | — | 100 | — |

[a]As the acetate
[b]EO conversion rate in grams of EO converted per hour
[c]3-hydroxy propanal Illustrative Embodiment II: Hydrogenation of Hydroformylation Product Ten grams of the reaction product from an ethylene oxide hydroformylation reaction such as example 5 above are charged to a 300 ml autoclave along with 40 grams of deionized water and 2 grams of Raney nickel catalyst. The autoclave is flushed with hydrogen, pressured with hydrogen to 1000 psig and heated to 110° C. for 5 hours. The autoclave is cooled to room temperature, vented of excess gas, and samples are removed for analysis by gas chromatography and mass spectroscopy. This analysis shows 1,3-propanediol as the major product in the water solution. The selectivity to 1,3- propanediol is about 90% with greater than 80% of 3-hydroxy-propanal being converted to the diol.

What is claimed is:

1. A process for making 3-hydroxypropanal which comprises intimately contacting
   (a) ethylene oxide,
   (b) ditertiary phosphine-modified cobalt carbonyl catalyst, said phosphine being of the formula

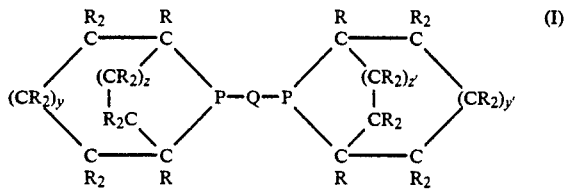

where Q represents hydrocarbylene of up to 30 carbon atoms; y and z represent zero or positive integers whose sum is from 2 to 7; y' and z', independent of the values of y and z, represent zero or positive integers whose sum is from 0 to 7; and R independently represents hydrogen and hydrocarbyl of from 1 to 30 carbon atoms,
   (c) catalyst promoter comprising an acid and a metal salt promoter selected from a salt of a metal of Group IIA, Group IIB, Group IIIB and the Rare Earth Series of the Periodic Table of the Elements (CAS version),
   (d) carbon monoxide, and
   (e) hydrogen, the molar ratio of carbon monoxide to hydrogen being from about 4:1 to about 1:6,
in liquid-phase solution in an inert reaction solvent, at a temperature of from about 30° C. to about 150° C. and a pressure of from about 50 psi to about 10,000 psi.

2. The process of claim 1 wherein in the phosphine y and z represent positive integers whose sum is from 2 to 7 and y' and z', independent of the values of y and z, represent positive integers whose sum is from 2 to 7.

3. The process of claim 2 wherein in the phosphine the sum of y and z is 3, each of which has a minimum value of 1, and the sum of y' and z' is 3, each of which has a minimum value of 1.

4. The process of claim 1 wherein the ratio of gram equivalents of acid promoter to gram atoms of cobalt in the catalyst ranges from about 0.001:1 to about 4:1 and the ratio of gram equivalents of alkali metal of the salt promoter to gram atoms of cobalt in the catalyst ranges from about 0.001:1 to about 2:1.

5. The process of claim 4 wherein the ratio of gram equivalents of acid promoter to gram atoms of cobalt in the catalyst ranges from about 0.01:1 to about 2:1 and the ratio of gram equivalents of alkali metal of the salt promoter to gram atoms of cobalt in the catalyst ranges from about 0.01:1 to about 1:1.

6. The process of claim 1 wherein the ratio of gram equivalents of metal of the salt promoter to gram atoms of cobalt in the catalyst ranges from about 0.1:1 to about 0.5:1.

7. The process of claim 3 wherein in the phosphine Q is selected from ethylene, propylene and butylene.

8. The process of claim 7 wherein in the phosphine Q is ethylene and the phosphorous to cobalt atom ratio in the catalyst ranges from about 0.5:1 to about 2:1.

9. The process of claim 8 wherein the phosphorous to cobalt atom ratio in the catalyst ranges from about 1:1 to about 1.5:1.

10. The process of claim 1 wherein the metal salt promoter is a salt of a metal selected from Mg, Ca, Sn, Zn, Y and La.

11. The process of claim 1 wherein the metal salt promoter is a salt of a metal selected from the Rare Earth Series.

12. The process of claim 1 wherein the product thereof is contacted with hydrogen in the presence of a hydrogenation catalyst at a temperature ranging from about 30° C. to about 175° C.

13. A process for making 3-hydroxypropanal which comprises intimately contacting
   (a) ethylene oxide,
   (b) ditertiary phosphine-modified cobalt carbonyl catalyst, said phosphine being a hydrocarbylene-bis(monophosphabicyclononane) in which each phosphorus atom is joined to hydrocarbylene and is a member of a bridge linkage without being a bridgehead atom and which hydrocarbylene-bis(-monophosphabicyclononane) has 18 to 80 carbon atoms, 8 carbon atoms thereof together with a phosphorus atom being members of each of the two bicyclic skeletal structures,
   (c) catalyst promoter comprising an acid and a metal salt promoter selected from a salt of a metal of Group IIA, Group IIB, Group IIIB and the Rare Earth Series of the Periodic Table of the Elements (CAS version),
   (d) carbon monoxide, and
   (e) hydrogen, the molar ratio of carbon monoxide to hydrogen being from about 4:1 to about 1:6,
in liquid-phase solution in an inert reaction solvent, at a temperature of from about 30° C. to about 150° C. and a pressure of from about 50 psi to about 10,000 psi.

14. The process of claim 12 wherein the ratio of gram equivalents of acid promoter to gram atoms of cobalt in the catalyst ranges from about 0.001:1 to about 4:1 and the ratio of gram equivalents of alkali metal of the salt promoter to gram atoms of cobalt in the catalyst ranges from about 0.001:1 to about 2:1.

15. The process of claim 14 wherein the ratio of gram equivalents of acid promoter to gram atoms of cobalt in the catalyst ranges from about 0.01:1 to about 2:1 and the ratio of gram equivalents of alkali metal of the salt promoter to gram atoms of cobalt in the catalyst ranges from about 0.01:1 to about 1:1.

16. The process of claim 13 wherein the ratio of gram equivalents of metal of the salt promoter to gram atoms of cobalt in the catalyst ranges from about 0.1:1 to about 0.5:1.

17. The process of claim 13 wherein in the phosphine the hydrocarbylene is selected from ethylene, propylene and butylene.

18. The process of claim 13 wherein in the phosphine the monophosphabicyclononane is selected from 9-phosphabicyclononane, 9-phosphabicyclononane and mixtures thereof.

19. The process of claim 13 wherein in the phosphine the hydrocarbylene is ethylene and the monophosphabicyclononane is selected from 9-phosphabicyclononane, 9-phosphabicyclononane and mixtures thereof.

20. A process for making 3-hydroxypropanal and 1,3-propanediol which comprises intimately contacting
   (a) ethylene oxide,
   (b) ditertiary phosphine-modified cobalt carbonyl catalyst, said phosphine being 1,2-bis(9-phosphabicyclononane)ethane and wherein the atom ratio of phosphorous to cobalt ranges from about 0.5:1 to about 2:1, (c) catalyst promoter comprising an acid and a metal salt promoter selected from a salt of a metal of Group IIA, Group IIB, Group IIIB and the Rare Earth Series of the Periodic Table of the Elements (CAS version) wherein the ratio of gram equivalents of acid promoter to gram atoms of cobalt in the catalyst ranges from about 0.001:1 to about 4:1 and the ratio of gram equivalents of metal of the salt promoter to gram atoms of cobalt in the catalyst ranges from about 0.001:1 to about 2:1, (d) carbon monoxide, and (e) hydrogen, the molar ratio of carbon monoxide to hydrogen being from about 4:1 to about 1:6, in liquid-phase solution in an inert reaction solvent, at a temperature of from about 30° C. to about 150° C. and a pressure of from about 50 psi to about 10,000 psi.

* * * * *